United States Patent [19]

Lewis et al.

[11] Patent Number: 5,325,862
[45] Date of Patent: Jul. 5, 1994

[54] METHOD AND/OR SYSTEM FOR PERSONAL IDENTIFICATION AND IMPAIRMENT ASSESSMENT FROM BRAIN ACTIVITY PATTERNS

[75] Inventors: Gregory W. Lewis, Solana Beach; David L. Ryan-Jones, San Diego, both of Calif.

[73] Assignee: The United States of America as represented by the Secretary of the Navy, Washington, D.C.

[21] Appl. No.: 39,596

[22] Filed: Mar. 26, 1993

[51] Int. Cl.[5] .......................................... A61B 5/0484
[52] U.S. Cl. .................................................. 128/731
[58] Field of Search ................ 128/731, 732, 745, 746

[56] References Cited

U.S. PATENT DOCUMENTS

| | | |
|---|---|---|
| 4,545,388 | 10/1985 | John . |
| 4,736,751 | 4/1988 | Gevins et al. . |
| 4,913,160 | 4/1990 | John . |
| 4,974,602 | 12/1990 | Abraham-Fuchs et al. ......... 128/732 |
| 4,984,578 | 1/1991 | Keppel et al. ....................... 128/732 |
| 4,993,068 | 2/1991 | Piosenka et al. . |
| 4,998,279 | 3/1991 | Weiss . |
| 5,092,343 | 3/1992 | Spitzer et al. . |

OTHER PUBLICATIONS

"Neural Network Architectures, An Introduction" by Judith E. Dayhoff, Title page and contents page.
"Event Related Brain Electrical And Magnetic Activity: Toward Predicting On-Job Performance" by Gregory W. Lewis pp. 159-182.
"Temporal Stability of Multichannel, Multimodal ERP Recording" by Gregory W. Lewis, pp. 131-144.
"Evoked Brain Activity and Personnel Performance" by Gregory W. Lewis et al., pp. 97-131.
"Few-Trial Evoked Field Stability Using The DC Squid" by G. Lewis et al., pp. 343-347.
"Evoked Neuromagnetic Fields": Implications For Indexing Performance, by G. W. Lewis et al., pp. 266-269.
"Temporal Variability of the Neuromagnetic Evoked Field: Implications For Human Performance Assessment", by G. W. Lewis et al., pp. 217-220.
"Parallel Distributed Processing, Explorations in the Microstructure of Cognition", title page, contents and preface.
"Recent Advances In EEG And EMG Data Processing", Statistical Analysis of Extracted Features by Paul Naitoh et al., pp. 179-194.
"Parallel Distributed Processing, Explorations in the Microstructure of Cognition, vol. 2: Psychological and Biological Models" by McClelland et al., title page, contents pages and preface.
"Neural Computing Theory and Practice" by Philip D. Wasserman, contents and preface.
"Electroencephalography and Clinical Neurophysiology" by H. Jasper, pp. 371-375.

*Primary Examiner*—George Manuel
*Attorney, Agent, or Firm*—Harvey Fendelman; Thomas Glenn Keough

[57] ABSTRACT

The invention provides an apparatus and method for identifying individuals based upon patterns of physiological activity generated in the brain and for distinguishing between normal and impaired brain states in any particular individual. These patterns may be obtained by directly or indirectly recording the electrical and/or magnetic activity associated with sensory, cognitive, and motor processing in the brain. This activity may be recorded using sensors placed in, on, or near the scalp. In this system, samples of individual brain activity are stored in an "intelligent" data base of a data acquisition/transformation stage which has the capability to learn to distinguish the individual characteristics of normal patterns of brain activity.

61 Claims, 4 Drawing Sheets

METHOD AND/OR SYSTEM FOR PERSONAL IDENTIFICATION AND IMPAIRMENT ASSESSMENT FROM BRAIN ACTIVITY PATTERNS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Individual identification and assessment are necessary for many purposes in society, such as for example, to control access to property and equipment. Currently, access to secured areas and computer systems has depended primarily upon security badges and passwords. However, both of these security methods can be subverted. New techniques are being investigated and developed for use as improved access control techniques. In addition to the traditional fingerprint, palm prints and photographs of the retina of the eye have also been used for identification purposes, yet these systems which rely on anatomical features. As in the case of fingerprints, these methods may be subverted. Biochemical systems such as genetic testing are being increasingly used for forensic testing, but are not practical at this time for access control purposes.

Thus, in accordance with this inventive concept a need has become apparent for an improvement upon the currently used techniques for individual identification and for distinguishing between the normal and impaired brain states of an individual.

SUMMARY OF THE INVENTION

The present invention is directed toward providing an apparatus for identifying an individual based upon patterns of physiological activity generated in the brain of the individual. A stimulator provides an initial or first controlled stimulation event for the individual to evoke a first event related response of physiological activity generated in the brain. In the context of this invention, the terms response and responses infer or imply evoked or event related potentials and/or event related magnetic fields. At least one sensor on the scalp or skin provides signals representative of the first event related response of the physiological activity generated in the brain. A data acquisition/transformation stage receives the signals representative of the first event related response of the physiological activity generated in the brain and is adapted to transform the representative signals into first pattern classification feature signals representative of the patterns of physiological activity generated in the brain of the individual. The data acquisition/transformation stage also provides memory for stored first pattern classification feature signals of the patterns of physiological activity generated in the brain of the individual. The stimulator provides a subsequent controlled stimulation event for the individual to evoke a subsequent event related response of the physiological activity generated in the brain. The sensor provides signals representative of the subsequent event related response of the physiological activity generated in the brain, and the data acquisition/transformation stage transforms the signals representative of the subsequent event related response of the physiological activity generated in the brain into subsequent pattern classification feature signals representative of the patterns of physiological activity generated in the brain of the individual. The data acquisition/transformation stage compares the stored pattern classification feature signals of the patterns of physiological activity generated in the brain of the individual with the subsequent pattern classification feature signals representative of the patterns of physiological activity generated in the brain of the individual to indicate the identification of the individual or to indicate that the individual has a brain impaired condition.

The data acquisition/transformation stage includes a neural network or a computer having a neural network being suitably programmed in accordance with neural network techniques, to transform the signals representative of the first and subsequent event related responses of the physiological activity generated in the brain to create, train and test the neural network to distinguish the first and subsequent pattern classification feature signals representative of the patterns of physiological activity generated in the brain of the individual.

Further in accordance with this inventive concept a method provides an identification of an individual based upon patterns of physiological activity generated in the brain of the individual. A first stimulating of the individual with a first controlled stimulation event evokes a first event related response of the physiological activity generated in the brain to permit an initial or first sensing of the signals representative of the first event related response of the physiological activity generated in the brain. An initial or first receiving is made of the signals representative of the first event related response of the physiological activity generated in the brain in a data acquisition/transformation stage. The data acquisition/transformation stage also makes a first transforming of the signals representative of the first event related response of the physiological activity generated in the brain into first pattern classification feature signals that are representative of the patterns of physiological activity generated in the brain of the individual to enable a storing thereof.

A subsequent stimulating of the individual with a subsequent controlled stimulation event for the individual evokes a subsequent event related response of the physiological activity generated in the brain. A subsequent sensing of the subsequent event related response of the physiological activity generated in the brain provides signals representative of the subsequent event related response of the physiological activity generated in the brain. Next, a subsequent transforming of the signals representative of the subsequent event related response of the physiological activity generated in the brain is made into subsequent pattern classification feature signals representative of the patterns of physiological activity generated in the brain of the individual in the data acquisition/transformation stage. A comparing of the stored pattern classification feature signals of the patterns of physiological activity generated in the brain of the individual with the subsequent pattern classification feature signals representative of the patterns of physiological activity generated in the brain of the individual in the data acquisition/transformation stage assures an identification of an individual or an indication of a brain impaired condition.

The first and subsequent transforming can be performed by a neural network provided in the data acquisition/transformation stage or a suitably programmed computer having a neural network in the data acquisition/transformation stage. In either case, the neural network transforms the signals representative of the first and subsequent event related responses of the physiological activity generated in the brain to create, train and test the neural network in accordance with known neural network modes of operation and neural network techniques. This transforming distinguishes the first and subsequent pattern classification feature signals representative of the patterns of physiological activity generated in the brain of the individual.

As a further option, the first stimulating may be by a series of controlled stimulation events for each individual that evokes a series of event related responses of the physiological activity generated in the brain. The sensor disposed on the scalp or skin of the individual now effects a sensing to provide a series of signals representative of the series of first event related responses of the physiological activity generated in the brain. The first transforming by the data acquisition/transformation stage transforms the series of signals representative of the first event related responses of the physiological activity generated in the brain into the first pattern classification feature signals representative of the patterns of physiological activity generated in the brain of the individual. Again, storing provides for the storage of the first pattern classification feature signals representative of the patterns of physiological activity generated in the brain of each individual.

An object of the invention is to provide an apparatus for, and method of, utilizing event related potential (ERP), and/or event related field (ERF), waveforms for classification purposes.

Another object of the invention is to provide an apparatus for, and method of, utilizing ERP and/or ERF morphology for personal identification.

Another object of the invention is to provide an apparatus for, and method of, personal identification relying on an individual's ERP and/or ERF pattern, or "brainprint", or "brain signature".

Another object of the invention is to provide an apparatus for, and method of, assessing job performance and/or functional impairment due to fatigue, stress, alcohol and drug abuse, and other factors.

Another object of the invention is to provide an apparatus for, and method of, assessing job performance and/or functional impairment due to fatigue, stress, alcohol and drug abuse, and other factors by the identification of critical changes in individual ERP and/or ERF patterns.

Another object of the invention is to provide an apparatus for, and method of, providing an individual identification system having applications for security/intelligence/interrogation, personnel reliability identification and assessment, neonatal and infant identification.

Another object of the invention is to provide an apparatus for, and method of, providing an individual identification system that is difficult to subvert because of its reliance on the use of physiological measures, for example, the use of brain activity resulting from sensory, cognitive and motor processing to identify individuals.

Another object of the invention is to provide an apparatus for, and method of, providing an individual identification system that is objective and very quickly performed by the utilization of neural network technology to classify ERP and/or ERF waveforms.

Another object of the invention is to provide an apparatus for, and method of, providing an individual identification system that would be able to take advantage of new and future brain technologies, such as brain mapping and imaging.

Another object of the invention is to provide an apparatus for, and method of, assessing job performance and/or functional impairment of an individual having applications for security/intelligence/interrogation, personnel reliability identification and assessment, neonatal and infant identification.

Another object of the invention is to provide an apparatus for, and method of, assessing job performance and/or functional impairment of an individual that is difficult to subvert because of its reliance on the use of physiological measures, for example, the use of brain activity resulting from sensory, cognitive and motor processing to identify individuals.

Another object of the invention is to provide an apparatus for, and method of, assessing job performance and/or functional impairment of an individual that is objective and very quickly performed by the utilization of neural network technology to classify ERP and/or ERF waveforms.

Another object of the invention is to provide an apparatus for, and method of, assessing job performance and/or functional impairment of an individual that would be able to take advantage of new and future brain technologies, such as brain mapping and imaging.

These and other objects of the invention will become more readily apparent from the ensuing specification and drawings when taken in conjunction with the appended claims.

DESCRIPTION OF THE PREFERRED EMBODIMENT

Figure 1:
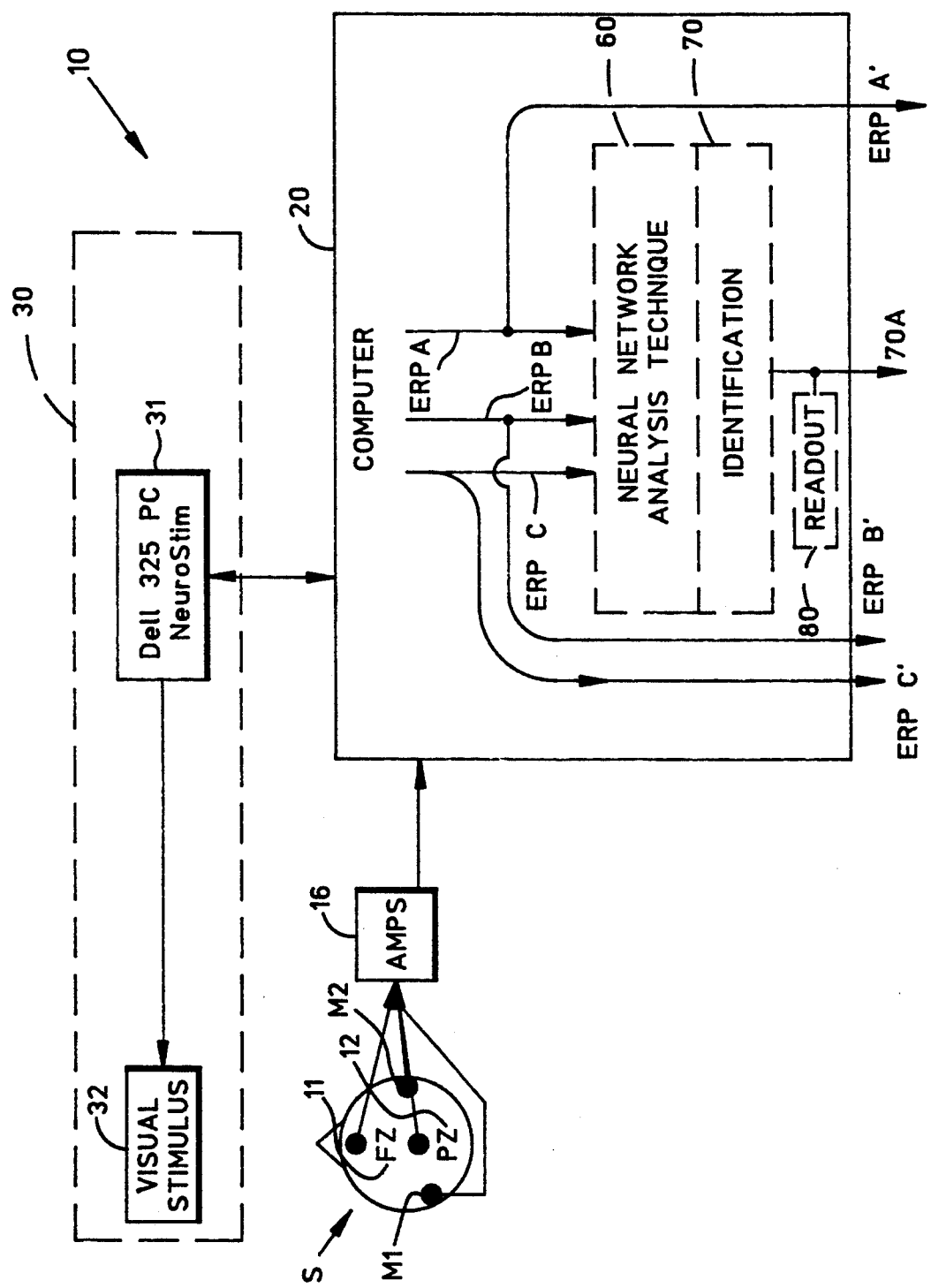
FIG. 1 shows a schematic representation of an overview of the hardware and software systems of the individual identification and/or impairment method/system.

For more than 50 years, the research literature has suggested that there are large individual differences in the electrical and magnetic activity in the brain. There is also evidence that some of the characteristics of brain activity may be relatively stable when measured from day to day. Brain responses to sensory stimulation (e.g. visual, auditory, somatosensory, olfactory, gustatory) as well as higher-order cognitive processing (e.g., decision-making), now can be examined in great detail using a variety of recording procedures. An ongoing record of brain electrical activity records is called an electroencephalogram (EEG), and a comparable record of magnetic activity is called a magnetoencephalogram (MEG). However, EEG and MEG records may show apparent "variation" beyond individual subject variation. Special techniques may be necessary to stabilize activity patterns. Brain activity can be stabilized by strict control of the conditions under which brain responses are generated. When human sensory systems are stimulated by an event such as a flash of light or a tone, there is a predictable sequence of processing that occurs in the brain. This processing generates an event-related potential (ERP) that can be recorded from the scalp beginning shortly after the onset of stimulation, and lasting for 1-3 seconds after the stimulation. These ERPs can be repeatedly generated from individuals given the same stimulus. Due to the low amplitude of the signal, it is often necessary to repeatedly sample the response to the stimulus, and to average the response patterns. ERP measures are in the microvolt range.

Comparable records of averaged magnetic activity are called evoked fields or event-related fields (ERFs). Neuromagnetic measures have only recently been made possible. Due to the low amplitude of the signal, currently special low-temperature, superconducting systems are required to measure the magnetic signals emitted by brain tissue. The magnetic unit of measurement is femtoTesla ($10^{-15}$ Tesla). New materials are being developed which will allow superconductivity at a much higher temperature resulting in decreased cost and increased availability of neuromagnetic equipment. Neuroelectric and neuromagnetic recordings are subsets of more general measures, called bioelectric and biomagnetic measures. Bioelectric and biomagnetic measures refer to recordings from many different types of tissue including neural, muscle, heart, and lungs.

ERP recordings have been shown to be stable and unique to individuals, see the articles by P. Naitoh and G. W. Lewis, "Statistical Analysis of Extracted Features," in *Recent Advances in EEG and EMG Processing*, edited by N. Yamaguchi and K. Fujisawa, editors, Elsevier/North Holland Biomedical Press, Amsterdam, 1981, pp. 179-194; by G. W. Lewis, "Temporal stability of multichannel, multimodal ERP recordings", *International Journal of Neuroscience*, 25, 131-144, (1984); and by D. L. Ryan-Jones and G. W. Lewis, "Neural network analysis of event-related potential (ERP) Data", in *Independent Research and Independent Exploratory Development Programs: FY91 Annual Report* (NPRDC Report AP-92-5), edited by W. E. Montague, Navy Personnel Research and Development Center, San Diego, 1992. Although the actual shape of an ERP varies considerably from individual to individual, there is stability within individuals over time for individual waveforms. Sources of ERP variation include individual differences in brain anatomy and differences in the way in which information is processed by the individual. Therefore, it is now feasible to demonstrate the use of "brain signatures" for security, intelligence, and other military and civilian purposes.

In accordance with this inventive concept ERP and/or ERF waveforms can be used as classifiers for several purposes. First, since ERP and/or ERF morphology is relatively unique to individuals, an individual's ERP and/or ERF pattern, or "brainprint", can be used for personal identification in a manner analogous to fingerprints. Second, because there is remarkable degree of stability in individual waveforms over time, it is possible to identify critical changes in individual ERP and/or ERF patterns which can be used to assess job performance and functional impairment due to fatigue, stress, alcohol and drug abuse, and other factors. Other potential uses of the individual identification system include security/intelligence/interrogation, personnel reliability identification and assessment, neonatal and infant identification.

Heretofore, one problem which has limited the interpretation and use of bioelectric and biomagnetic data is the sheer complexity of the brain networks which generate the data. There are numerous neural networks in the brain, and these networks have very complex interconnections and nonlinear response patterns. Relationships between the latencies and amplitudes of ERP and ERF waveform features are becoming increasingly well understood. In addition, there are many individual variations in waveform morphology which complicate the identification of specific waveform features.

Recently, new computing techniques which are modeled after brain neural functioning have been developed. As a general class, these are called neural network analysis techniques. The neural network analysis technology offers a method for finding complex, nonlinear relationships in large data sets, even when the nature of the relationships is not known in advance. Neural network technology is most often implemented using computer software programs, but hardware implementations of the technology are also available. Neural network theory, and detailed descriptions of specific techniques are available in numerous books and articles, see, for example, the theory and technique information by J. Dayhoff, *Neural Network Architectures: An Introduction* New York: Van Nostrand Reinhold, (1990); by D. E. Rumelhart & J. L. McClelland, *Parallel Distributed Processing. Volume 1: Foundations*, Cambridge: The MIT Press, (1986); by J. L. McClelland and D. E. Rumelhart, *Parallel Distributed Processing. Vol. 2: Psychological and Biological Models*, The MIT Press, Cambridge, 1986; and by P. Wasserman, *Neural Computing: Theory and Practice*, van Nostrand Reinhold, New York, 1989. A unique feature of this technology is the capability to learn which features of a data set can be used to classify the examples into either unknown or predetermined categories. There are a variety of neural network techniques which could be used to classify ERP or ERF patterns. Neural networks may differ in the way the elements are interconnected, the way the data are processed, as well as the way in which the network structure is modified during learning. In most networks, input data values are adjusted through a series of layers by a series of transforms and weights so that the output category is correctly predicted. For example, if all of the possible examples are contained in the data set, then a self-organizing network could be used to classify the brainwave data. If only some of the possible examples are in the data set, then a network which utilized supervised learning could be more appropriate. The most commonly used and best described network is the backpropagation network. This network is named because the error in output classification is used to adjust the weights at each level in the network in a backward fashion.

In accordance with this inventive concept, known facts, as well as old and new technologies, are applied for the first time in a unique way. Some of the key components include sensors which are attached or otherwise suitably disposed adjacent to the scalp or skin, a neuroelectric or neuromagnetic recording system consisting of a computer (e.g. personal, mini or mainframe), signal amplifiers and/or filters, software for data acquisition, processing, analysis and display, and neural network hardware and/or software.

Referring now to the drawings, FIG. 1 shows an overview of the hardware and software system 10 for identifying individuals and/or for distinguishing between normal and impaired brain states in any particular individual based upon patterns of physiological activity generated in the brain. An individual subject S to be tested for identification purposes or for distinguishing between normal and impaired brain states has at least one sensor, in this case, two electrodes 11 and 12 placed on the scalp in association with a reference electrode, or magnetic sensors appropriately mounted above the scalp recording sites. The electrodes selected for this purpose may be commercially available units such as those commercially marketed by Electro-Cap International 1300 North Barron Street, Box 87, Saxton Ohio 45320, which may be made of tin to minimize depolarization. The electrodes are attached to the scalp using a suitable electrolyte material which also is commercially available from a number of sources such as Electro-Cap International. A wide variety of electrodes or sensors fabricated from a number of appropriate materials may be selected to provide the monitored potentials (or monitored magnetic signals in the case of magnetic sensing) that conform to the standards of the 10/20 International System, see for example, the article by H. Jasper, "The ten-twenty electrode system of the International Federation", *Electroencephalography and Clinical Neurophysiology*, 10, 371-375, (1958).

In accordance with this invention, the signals received by the sensors have been termed response and responses to infer or imply evoked or event related potentials and/or event related fields. While a pair of electrodes are referred to in this illustrative embodiment, it is to be understood that one skilled in the art to which this invention pertains could select any number or models and configurations of electrodes or magnetic sensors, or combinations of electrodes and magnetic sensors, and appropriately apply them to gather the signals of physiological activity in the brain without departing from the scope of this inventive concept. Furthermore, it is apparent to one of ordinary skill in the art that the location of the electrodes and magnetic sensors could be changed to appropriately monitor the relevant brain tissue emitting electrical and magnetic signals of physiological activity in the brain for arriving at a suitable patterning for a desired purpose, such as, but not limited to identification and/or an impaired condition.

Sensing electrodes 11 and 12 are located at the parietal (PZ) and frontal (FZ) sites were each referenced to electrode M1 disposed on the left mastoid region, using two separate amplifiers. An additional amplifier recorded electrical voltage from M1 referenced to electrode M2 disposed on the right mastoid area. The electrical activity from M1 and M2 were averaged through software in a common technique called digital re-referencing. Re-referencing was done to obtain an "average" reference from the brain.

The electrical voltage picked up by the electrodes produced by physiological activity in the brain is very small, in the microvolt range, and must be amplified and filtered by a amplifier stage 16. The amplifier stage is made up of typically, one amplifier for each electrode and its reference. A typical amplifier is a Model 12A5 by the Grass Co., Quincy Mass. 02169 that not only amplifies the sensed signals but also provides for a degree of filtering of unwanted signals.

To ensure adequate recording attachment of the electrodes, the impedance of each electrode is measured prior to recording using a Grass Co. Impedance meter, model EZMID. Typical meter readings should be 5000 ohms or less. The electrode impedance provides an index of how well the electrodes are attached to the scalp. Impedances greater than about 5000 ohms suggests that adequate electrical contact has not been obtained, and would allow "noise" such as 60 Hz line voltage to contaminate the recordings. Amplifier gain of the amplifier stage is about 20000 and the filter bandpass setting is about 0.1-100 Hz for each of the sensed signals. The gain of 20000 is used to take an average 50 microvolt signal up to about 1 volt for adequate input to the analog-to-digital converter in a computer in a data acquisition/transformation stage (or transformer stage) 20.

The amplified signals representative of physiological activity in the brain from amplifier stage 16 are coupled to data acquisition/transformation stage 20 that includes a Dell model 325 personal computer (PC). The PC of the data acquisition/transformation stage is based on an Intel 386 CPU chip and runs at 25 MHZ, has 8 Mbytes of random access memory, a 1 Gbyte hard disk, MSDOS 5.0 operating system, 14" VGA display monitors (0.28" dot pitch), a monitor for the experimenter/operator, and a monitor for presenting the visual stimuli to the subject. It is apparent to one skilled in the art that a variety of other electrodes, amplifiers, filters, impedance meters, and computers, disks, memory, operating systems and monitors could have been selected having other suitable capabilities other than those specifically identified above to appropriately process the incoming signals representative of physiological activity in the brain in accordance with this inventive concept.

The analog data representative of the sensed physiological activity in the brain are sampled, converted to digital format, and analyzed using suitable hardware and software well known to one skilled in the art to which this invention pertains. A NeuroScan, Inc. SCAN hardware and software subsystem of NeuroScan, Inc. of 1035 Sterling Road, Suite 103, Herndon, Va. 22070-3806 was selected for the PC to provide the desired sampling, conversion to digital format, and analysis in accordance with this inventive concept. Sampling rate of the NeuroScan, Inc. SCAN is typically 128 Hz. In accordance with teachings disclosed herein one skilled in the art to which the invention pertains can select from the many commercially available other data sampling, conversion and storage devices and software packages and processing schemes to practice this inventive concept.

A visual/audio stimulator stage, or visual stimuli stage 30 is electronically coupled to data acquisition/transformation stage 20 and includes a second PC 31 (Dell, model 325) coupled to a video monitor 32 to primarily function as a visual stimulator. The PC part of the visual stimuli stage and has a similar configuration to data acquisition/transformation stage 20 except that it is provided with a 340 Mbyte hard disk that is coupled to the PC of data acquisition/transformation stage 20 through suitable interface hardware and software commercially available by NeuroScan, Inc. as NeuroStim.

Visual stimuli stage 30 provides the visual stimuli in synchronization with the data gathering of the event related responses by the electrodes and processing of data acquisition/transformation stage 20, such as light flashes or selected short duration images that are presented for subject S via video monitor 32 which has the capability to give many options for stimulus presentation including auditory, psychomotor, complex cognitive tasks, or other scenarios which may be developed by the user. It is apparent to one skilled in the art to which this invention pertains that other appropriate software and stimulus could have been chosen to provide the required stimulus information.

The NeuroScan SCAN hardware and software in data acquisition/transformation stage 20 effects a first signal transformation to provide a sampled and converted to digital format signals ERP A. The ERP A signals may be the form of the signals which are provided for subsequent processing that will accomplish the desired end result, such as an identification among a particular group of subjects, for example. The NeuroScan SCAN software in data acquisition/transformation stage 20 also has the capability to effect another signal transformation to provide processed event-related brain potentials therein or, optionally, as output signals ERP B, such as by removing unwanted artifacts such as produced by eye blink or muscle movement. The NeuroScan SCAN software in data acquisition/transformation stage 20 then effects a second transformation of the event related response signals to provide the selecting of specific single epochs used in ERP averages, event-related potential average signals ERP C. The ERP data were "windowed" in data acquisition/transformation stage 20 in order to reduce the number of inputs to the neural network to be described. Windowing refers to taking a specific number of points, such as 6, along the ERP waveform, either ERP A, ERP B or ERP C, and averaging them together, for example. These processes are well established and documented in the literature, such as Experimenters Workbench by Brainwave Systems Inc., 3400 Industrial Lane, Suite 3 Broomfield, Colo. 80020; Venus: SA by Neuroscientific Corp. 139 Florida Street, Farmingdale N.Y. 11735; SPECTRUM 32, by Cadwell Laboratories, 909 North Kellogg St., Kennewick Wash. 99336 etc.

Similar equipment and procedures to those referred to above are used in the recording, processing and analyzing of signals representative of physiological activity generated in the brain when they are in the form of neuromagnetic evoked field (EF) data. One skilled in the art to which this invention pertains, having the teachings disclosed herein, would merely select the suitable commercially available components associated with magnetic sensing along with data acquisition/transformation stage 20 and visual stimuli stage 30 to accommodate the desired application. Descriptions of appropriate hardware and software recording equipment and procedures associated with magnetic sensing have been published in the open literature, see, for example, the articles by G. W. Lewis, "Event-related brain electrical and magnetic activity: Toward predicting on-job performance", *International Journal of Neuroscience,* 18, 159–182, (1983); by G. W. Lewis, M. Blackburn, P. Naitoh, & M. Metcalfe, "Few-trial evoked stability using the DC SQUID" In Weinberg, H., Stroink, G , & Katila, T. *Biomagnetism: Applications and Theory,* New York: Pergamon Press, (1985); by G. W. Lewis, L. J. Trejo, P. Nunez, H. Weinberg, & P. Naitoh, "Evoked neuromagnetic fields: Implications for indexing performance" In Atsumi, K., Kotani, M., Ueno, S., Katila, T., & Williamson, S. J. *Biomagnetism* ~87 Tokyo: Tokyo Denki University Press, (1987); by G. W. Lewis, & R. C. Sorenson, R.C., "Evoked brain activity and personnel performance", In Dillon, R. F. & Pellegrino, J. W. *Testing, Theoretical and Applied Perspectives,* New York: Praeger, (1989); and by G. W. Lewis, L. J. Trejo, P. Naitoh, M. Blankenship & M. Inlow, "Temporal variability of the neuromagnetic evoked field: Implications for human performance assessment", In Williamson, S. J., Hoke, M., Stroink, G., & Kotani, M. *Advances in Biomagnetism,* New York: Plenum Press, (1989). These publications reported on data using a single channel neuromagnetometer; however, a multichannel neuromagnetometer system (BTI model 605) for the recording of EF and ERF data over more channels and larger number of brain regions is provided for as being in accordance with this inventive concept. Although the example herein provided concerns itself with processing only ERP, EF and ERF data could have been selected since it may provide improved identification due to being non-contact in nature, monopolar, improved localization of brain activity, and improved sensitivity to individual subject differences, please note the above identified article to Lewis, (1983).

The data processing described above that included the ERP processing and averaging might also include other data manipulations that would allow the data to be differently processed and/or enhanced by a variety of data processing procedures to make the sensed signals representative of physiological activity in the brain amenable to utilization in accordance with this inventive concept. Such data processing variations will readily suggest themselves to the routineer within the scope of this invention.

Neural network analysis 60 and the providing of identification 70 via a video monitor or graphic readout 80, for example, or an information output of identification patterns 70A for associated equipments are performed in association with the PC of data acquisition/transformation stage 20 either by a hardwired neural network fabricated in accordance with techniques and a configurations well known to the art, or, in the PC of data acquisition/transformation stage 20 by the programming therein of suitable commercially available software. The commercial software BrainMaker Professional, (BP), version 2.02, December, 1990, Version 2.51 Netmaker 1992, and/or Version 2.52 BrainMaker Professional available from California Scientific Software, 10024 Newtown Road, Nevada City Calif. 95959 were selected to create, train and test the neural network in the PC of data acquisition/transformation stage 20, (other software packages, freely available from a number of commercial sources could have been selected for this task, such as NeuroShell by Ward Systems Inc., 245 West Patrick Street, Fredrick Md. 21701; NeuralWorks Professional II, by NeuralWare Inc., Penn Center West, Building IV, Suite 227, Pittsburgh Pa. 15276; and ExploreNet 3000 by HNC Inc., 5501 Oberlin Drive, San Diego Calif. 92121-1718, for example.) The BP package includes the NetMaker software package to convert the ERP A, ERP B and ERP C data file into a BrainMaker network definition file and a fact file. The definition file gives specifications on how to build the network, the number of input, hidden and output neurons, the data type, and information about screen display. The fact .file specifies the input and training pair pattern information. Training of the network is done using a backpropagation learning algorithm, which result in trained network files. After training of the network is complete, running (testing) fact files are created.

The ERP A, ERP B and ERP C signals were appropriately internally routed in data acquisition/transformation stage 20 to assure that the signal transformations associated with the neural network analysis of these signals and the providing of identification patterns from these signals would progress. ERP A, ERP B and ERP C signals and identification patterns signals 70A information were provided as additional outputs from data acquisition/transformation stage 20 as identification patterns signals ERP A′, ERP B′, ERP C′ and identification patterns signals 70A for use and further processing by other interconnected computers that may be, for example, in a network of stations that require an immediate identification or impairment screening of personnel.

Identification and/or impairment screening of a subject is performed relatively fast. The subject's initial, first or past identification pattern is retrieved from data acquisition/transformation stage 20 and compared to a present or subsequent pattern of physiological activity generated in the brain that is sensed from the subject when the subject is to be later tested for the identification or impairment determination. A visual readout may be provided by a screen.

Figure 2:
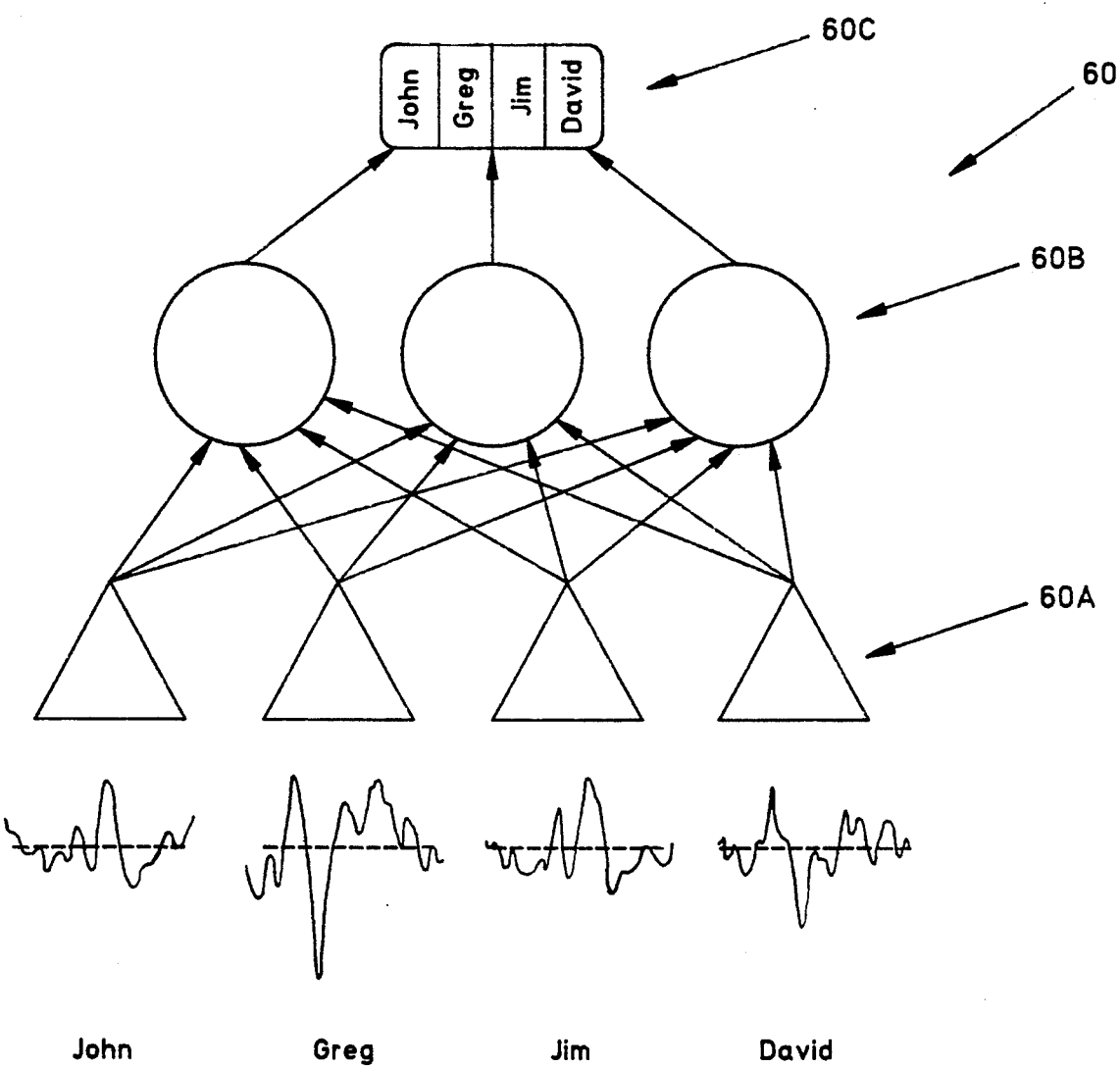
FIG. 2 shows a graphic representation of the process for making decisions about any new sample of event related potentials, ERP and/or event related fields, ERF once the neural network has been trained (four ERP data samples are depicted being processed by the neural network).

Referring to FIG. 2, a 3-layer backpropagation network 60 in PC data acquisition/transformation stage 20 having an input layer 60A, a hidden layer 60B, and an output layer 60C may be sufficient if the data set is relatively small (e.g., less than 100 individuals in the data base). The network may only require a single hidden layer with the same number of processing elements as inputs. One important step is the training and testing of the network. Half of the ERPs from the sample are used to train the neural network to distinguish between each individual. The other half of the ERPs are used to verify that the neural network is performing at the required level. Once the neural network has been trained, the network can be used to make decisions about any new sample of ERPs. This process is shown graphically in FIG. 2. Samples of ERP data from four (4) individuals, named John, Greg, Jim and David, are processed by the neural network. Identification of the individuals is shown at output layer 60C.

A preliminary test using neural network analysis of ERP patterns performed on 35 males had each subject perform 400 trials of a two-letter ("o" and "c") discrimination task. ERP data were recorded from site PZ referenced to the digitally-linked mastoid regions. Site PZ is located over the parietal region of the brain, which is believed to be a sensory association/integration area. The ERPs were sampled from −200 ms prestimulus to 1000 ms poststimulus at 128 Hz, 20000 amplifier gain, and 0.1–100 Hz filter bandpass. The ERP data were divided into 8 blocks of 50 trials (400 total). The first ten (10) trials in each block with correct behavioral responses (hits) were averaged by conventional methods to obtain 8 ERPs for each of the 35 subjects (280 ERPs total). The ERPs were divided into 25 windows which were about 47 ms wide, by averaging 6 data points in each window. A backpropagation network was used to classify the ERP data. The 3-layer network consisted of an input layer with 25 elements (ERP windows), a hidden layer with 25 elements, and an output layer with 35 elements (individual subjects).

The ERPs for the subjects were divided into training and test sets. The training set consisted of the ERP data from the odd-numbered blocks, and the test set consisted of the ERP data from the even-numbered blocks. All of the examples in the training set (4 ERPs for each of the 35 subjects) were correctly learned by the backpropagation network to the required criterion. The neural network was then tested using the different ERPs from the test set. The network correctly classified 70/140 (50%) of the ERPs based on the highest output value. These results were statistically significant given that each of the 35 subjects was a separate output category. An additional metric was used to evaluate the correctness of classification for the subjects. To be considered to be correctly classified, the network must assign the highest output value to 2 of the 4 ERP samples. Therefore, the network correctly classified 29/35 (83%) of the subjects.

Findings from the preliminary test were used to modify the apparatus/method of this inventive concept which was tested using ERP data from 40 different male subjects. Subjects were not preselected on any factor, including task or job performance. Data from a sensor from an additional recording site over the frontal region of the brain (FZ) was added to the data from Pz to allow for more classification features. Recording and averaging of the ERP records were the same noted in the two preceding paragraphs. However, the 5 prestimulus windows for each site were deleted from the data set. The study used 320 ERPs total (8 ERPs/subject × 40 subjects = 320 ERPs). There were 160 ERPs in each of the training and testing sets. The 3-layer neural network consisted of an input layer of 40 elements (20 ERP windows from each site), a hidden layer with 40 elements, and an output layer with 40 elements (subjects). All of the ERPs were correctly classified during training, and a substantial improvement in the classification of the test examples was seen during testing. The network correctly classified 117/160 (73%) ERPs in the test set. The classification described above showed that 39/40 (97.5%) of the subjects were correctly classified by the criterion of at least two of four ERPs for each individual.

Although at the present there are no other known ways to record brain function, in a practical way, other than neuroelectric contact electrodes or neuromagnetic pickup sensors, it is envisioned that other brain function sensors may evolve and be applicable to this inventive concept. Positron emission tomography (PET) technology is able to describe anatomical relationships and some physiological processing. However, PET is very expensive and may need improvement in temporal resolution for effective assessment of cognitive processing to lessen the several minutes of data recording required to show brain processing. PET is also an "active" technology requiring the injection of labeled radioisotopes to function. The ERP/ERF technology of this inventive concept is totally "passive," in that no energy or material need be injected or inserted in subjects to obtain the ERP/ERF data. Alternative technologies such as computerized axial tomography (CAT) and magnetic resonance imaging (MRI) are possible candidates for the proposed identification system, but are extremely expensive, and are "active" systems.

Figure 3A:
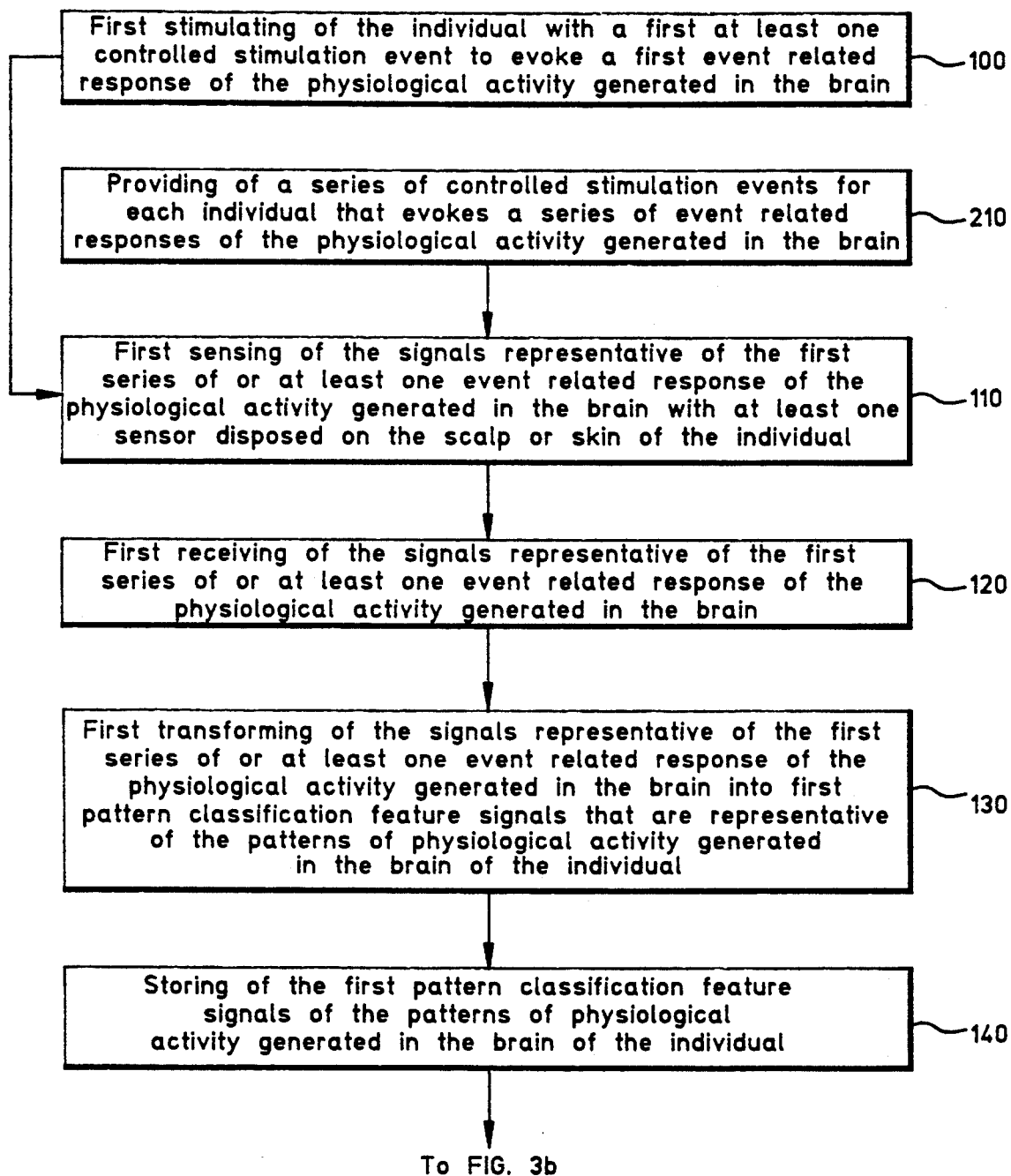
FIGS. 3a and 3b depict a method of the invention.
Figure 3B:
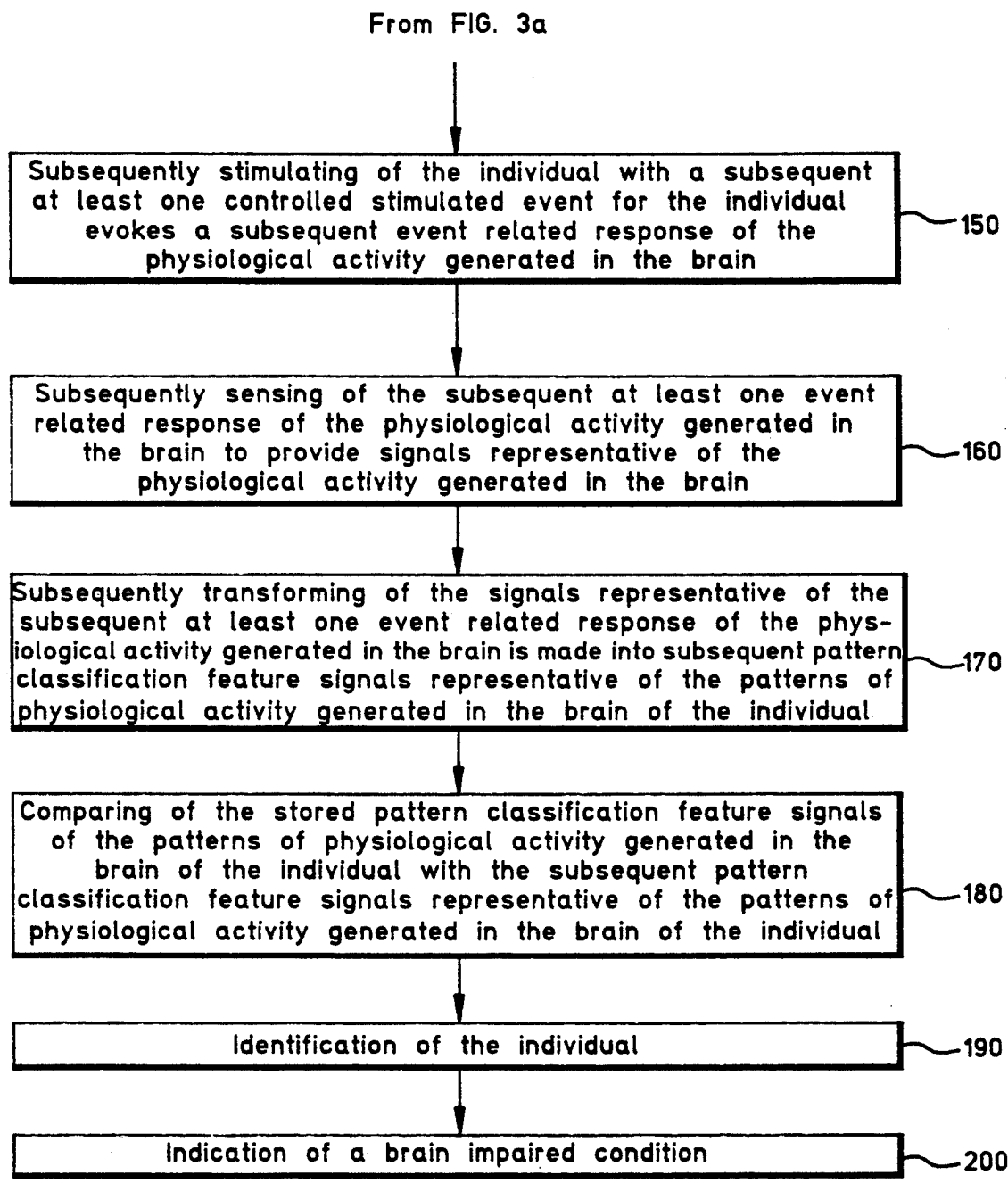

Referring to FIGS. 3a and 3b, in accordance with this inventive concept the disclosed apparatus assures a method that provides an identification of an individual based upon patterns of physiological activity generated in the brain of the individual. A first stimulating 100 of the individual with a first controlled stimulation event evokes a first event related response of the physiological activity generated in the brain. This permits an initial or first sensing 110 of the signals representative of the first event related response of the physiological activity generated in the brain with at least one sensor 11, 12 etc., disposed on the scalp or skin of the individual and an initial or first receiving 120 of the signals representative of the first event related response of the physiological activity generated in the brain in a data acquisition/transformation stage 20. In the data acquisition/transformation stage a first transforming 130 of the signals representative of the first event related response of the physiological activity generated in the brain is made into first pattern classification feature signals that are representative of the patterns of physiological activity generated in the brain of the individual. A providing of memory or storing 140 of the first pattern classification feature signals of the patterns of physiological activity generated in the brain of the individual is useful for later utilization.

The later utilization of the stored data is provided for by a later substantial repeat of the process above. A subsequent stimulating 150 of the individual with a subsequent controlled stimulation event for the individual evokes a subsequent event related response of the physiological activity generated in the brain. A subsequent sensing 160 of the subsequent event related response of the physiological activity generated in the brain provides signals representative of the subsequent event related response of the physiological activity generated in the brain. Next, a subsequent transforming 170 of the signals representative of the subsequent event related response of the physiological activity generated in the brain is made into subsequent pattern classification feature signals representative of the patterns of physiological activity generated in the brain of the individual in the data acquisition/transformation stage. A comparing 180 of the stored pattern classification feature signals of the patterns of physiological activity generated in the brain of the individual with the subsequent pattern classification feature signals representative of the patterns of physiological activity generated in the brain of the individual in the data acquisition/transformation stage assures an identification 190 of the individual. This procedure and comparing also can provide an indication 200 of a brain impaired condition.

The first and subsequent transforming can be performed by a neural network provided in the data acquisition/transformation stage, or the first and subsequent transforming is performed by a suitably programmed computer having a neural network in the data acquisition/transformation stage. The neural network transforms the signals representative of the first and subsequent event related responses of the physiological activity generated in the brain to create, train and test the neural network in accordance with known neural network operating techniques. This transforming distinguishes the first and subsequent pattern classification feature signals representative of the patterns of physiological activity generated in the brain of the individual.

The first stimulating may be the providing 210 of a series of controlled stimulation events for each individual that evokes a series of event related responses of the physiological activity generated in the brain. The first sensing by a sensor disposed on the scalp or skin of the individual now provides a series of signals representative of the series of first event related responses of the physiological activity generated in the brain. The first transforming by the data acquisition/transformation stage transforms the series of signals representative of the first event related responses of the physiological activity generated in the brain into the first pattern classification feature signals representative of the patterns of physiological activity generated in the brain of the individual. Again, as described above the providing of memory (or storing) is essentially the same to provide for the storage of the pattern classification feature signals representative of the patterns of physiological activity generated in the brain of each individual.

In addition to the analysis technique described above, the traditional statistical techniques are an alternative to neural network analysis. However, many assumptions must be made of the data, and these techniques may be insensitive to nonlinear processes. Neural network techniques do not make a priori assumptions about the input data, and are sensitive to nonlinear characteristics, which are found in biological recordings. As a result, neural networks consistently provide greater accuracy in the classification of complex, nonlinear data than the traditional statistical techniques.

The identification and impairment detection of this invention relies upon the use of physiological measures, and the utilization of neural network classification. The use of brain activity resulting from sensory, cognitive and motor processing to identify individuals avoids the problems associated with existing identification technology which assesses only anatomical features, such as the fingerprint, retinal and other anatomical features since it would be extremely difficult, if not impossible, to subvert brain recordings. Even though fingerprints are reliable, they can be disguised or subverted by using sandpaper or mild acid on the skin. Retinal features are not subvertable, but do not provide an indication of processing unless there is manifest abnormality visible on the retina, such as tumor or burn. The use of neural network technology to classify ERP and/or ERF waveforms provides a clear advantage of the identification and impairment detection capabilities of this inventive concept since all processing can be done objectively and very quickly. Once the neural network has been trained to identify an individual, the testing an ERP and/or ERF can be done in a matter of milliseconds. This identification apparatus/method would be able to take advantage of new and future brain technologies, such as brain mapping and imaging.

Obviously, many modifications and variations of the present invention are possible in the light of the above teachings. It is therefore to be understood that within the scope of the appended claims, the invention may be practiced otherwise than as specifically described.

We claim:

1. An apparatus for identifying an individual based upon data representing at least one pattern of physiological activity generated in the brain of said individual comprising:
   a stimulator located with respect to said individual to provide a first stimulation event which includes at least one stimulus for said individual to evoke a first event related pattern of physiological activity generated in the brain;
   at least one sensor adapted to be operatively disposed with respect to the scalp or skin of said individual that provides signals representative of said first event related pattern of physiological activity generated in the brain; and
   a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual, said data acquisition/transformation stage being further adapted to provide a memory to store said first pattern classification feature signals of said first event related pattern of physiological activity generated in the brain of said individual, said stimulator being adapted to provide a subsequent stimulation event which includes at least one stimulus for said individual to evoke a subsequent event related pattern of physiological activity generated in the brain, said at least one sensor being adapted to be operatively disposed with respect to the scalp or skin of said individual to provide signals representative of said subsequent event related pattern of physiological activity generated in the brain and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate the identification thereof.

2. An apparatus according to claim 1 in which said at least one sensor is at least one pair of a sensor electrode and a reference electrode for sensing event-related potentials.

3. An apparatus according to claim 1 in which said at least one sensor is a plurality of pairs of sensor electrodes and reference electrodes for sensing event-related potentials.

4. An apparatus according to claim 1 in which said at least one sensor is at least one sensor coil for sensing event-related fields.

5. An apparatus according to claim 1 in which said at least one sensor is a plurality of sensor coils for sensing event-related fields.

6. An apparatus for indicating a brain impaired condition of an identified individual based upon data representing at least one pattern of physiological activity generated in the brain of said individual comprising:
  a stimulator located with respect to said individual to provide a first stimulation event which includes at least one stimulus for said individual to evoke a first event related pattern of physiological activity generated in the brain;
  at least one sensor adapted to be operatively disposed with respect to the scalp or skin of said individual that provides signals representative of said first event related pattern of physiological activity generated in the brain; and
  a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual, said data acquisition/transformation stage being further adapted to provide a memory to store said first pattern classification feature signals of said first event related pattern of physiological activity generated in the brain of said individual, said stimulator being adapted to provide a subsequent stimulation event which includes at least one stimulus for said individual to evoke a subsequent event related pattern of physiological activity generated in the brain, said at least one sensor being adapted to be operatively disposed with respect to the scalp or skin of said individual to provide signals representative of said subsequent event related pattern of physiological activity generated in the brain and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate a brain impaired condition of said individual.

7. An apparatus according to claim 1 or 6 in which said stimulator provides a first series of stimulation events to evoke a first series of event related patterns of physiological activity generated in the brain, said at least one sensor adapted to be operatively disposed with respect to the scalp or skin of said individual provides a first series of signals representative of said first series of first event related patterns of physiological activity generated in the brain and said data acquisition/transformation stage coupled to receive said first series of signals representative of said first series of first event related patterns of said physiological activity generated in the brain is adapted to transform said first series of signals representative of said first event related patterns of physiological activity generated in the brain into first patterns classification feature signals representative of said first event related patterns of physiological activity generated in the brain of said individual, said data acquisition/transformation stage being further adapted to store said first classification feature signals of said individual.

8. An apparatus according to claim 6 in which said at least one sensor is at least one pair of a sensor electrode and a reference electrode for sensing event-related potentials.

9. An apparatus according to claim 6 in which said at least one sensor is a plurality of pairs of sensor electrodes and reference electrodes for sensing event-related potentials.

10. An apparatus according to claim 6 in which said at least one sensor is at least one sensor coil for sensing event-related fields.

11. An apparatus according to claim 6 in which said at least one sensor is a plurality of sensor coils for sensing event-related fields.

12. A method of identifying an individual based upon data representing at least one pattern of physiological activity generated in the brain of said individual comprising:

- a first stimulating of said individual with a first stimulation event which includes at least one stimulus to evoke a first event related pattern of physiological activity generated in the brain;
- a first sensing of signals representative of said first event related pattern of physiological activity generated in the brain with a sensor adapted to be operatively disposed with respect to the scalp or skin of said individual;
- a first receiving of said signals representative of said first event related pattern of physiological activity generated in the brain in a data acquisition/transformation stage;
- a first transforming of said signals representative of said first event related pattern of physiological activity generated in the brain into first pattern classification feature signals representative of said pattern of physiological activity generated in the brain of said individual in said data acquisition/transformation stage;
- providing memory in said data acquisition/transformation stage to store said first pattern classification feature signals of said first event related pattern of physiological activity generated in the brain of said individual;
- subsequently stimulating said individual with a subsequent stimulation event which includes at least one stimulus for said individual to evoke a subsequent event related pattern of physiological activity generated in the brain, said first stimulation event and said subsequent stimulation event being substantially the same stimulus;
- subsequently sensing said subsequent event related pattern of physiological activity generated in the brain with said sensor adapted to be operatively disposed with respect to the scalp or skin of said individual to provide signals representative of said subsequent event related pattern of physiological activity generated in the brain;
- subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and
- comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate the identification thereof.

13. A method of indicating a brain impaired condition of an identified individual based upon data representing at least one pattern of physiological activity generated in the brain of said individual comprising:

- a first stimulating of said individual with a first stimulation event which includes at least one stimulus to evoke a first event related pattern of physiological activity generated in the brain;
- a first sensing of signals representative of said first event related pattern of physiological activity generated in the brain with a sensor adapted to be operatively disposed with respect to the scalp or skin of said individual;
- a first receiving of signals representative of said first event related pattern of physiological activity generated in the brain in a data acquisition/transformation stage;
- a first transforming of said signals representative of said first event related pattern of physiological activity generated in the brain into first pattern classification feature signals representative of said pattern of physiological activity generated in the brain of said individual in said data acquisition/transformation stage;
- providing memory in said data acquisition/transformation stage to store said first pattern classification feature signals of said first event related pattern of physiological activity generated in the brain of said individual;
- subsequently stimulating said individual with a subsequent stimulation event which includes at least one stimulus for said individual to evoke a subsequent event related pattern of physiological activity generated in the brain, said first stimulation event and said subsequent stimulation event being substantially the same stimulus;
- subsequently sensing said subsequent event related pattern of physiological activity generated in the brain with a sensor adapted to be operatively disposed with respect to the scalp or skin of said individual to provide signals representative of said subsequent event related pattern of physiological activity generated in the brain;
- subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and
- comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate a brain impaired condition thereof.

14. An apparatus for identifying an individual based upon data representing at least one pattern of physiological activity generated in the brain of said individual comprising:

- a stimulator located with respect to said individual to provide a first stimulation event which includes at least one stimulus for said individual to evoke a first event related pattern of physiological activity generated in the brain;
- at least one sensor adapted to be operatively disposed with respect to the scalp or skin of said individual that provides signals representative of said first event related pattern of physiological activity generated in the brain; and
- a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual, said data acquisition/transformation stage being further adapted to provide a memory to store said first pattern classification feature signals of said first event related pattern of physiological activity generated in the brain of said individual to indicate the identification thereof, said stimulator being adapted to provide a subsequent stimulation event which includes at least one stimulus for said individual to evoke a subsequent event related pattern of physiological activity generated in the brain, said at least one sensor being adapted to be operatively disposed with respect to the scalp or skin of said individual to provide signals representative of said subsequent event related pattern of physiological activity generated in the brain and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate the identification thereof, said data acquisition/transformation stage includes a neural network adapted to transform said signals representative of said first event related pattern of physiological activity generated in the brain and said subsequent event related pattern of physiological activity generated in the brain to create, train and test said neural network to distinguish said first pattern classification features signals and said subsequent pattern classification features signals of said individual.

15. An apparatus according to claim 14 in which said neural network of said data acquisition/transformation stage is adapted to transform said signals representative of said first event related pattern of physiological activity generated in the brain and subsequent event related pattern of physiological activity generated in the brain from a plurality of individuals to create, train and test said neural network to distinguish said first pattern classification features signals and said subsequent pattern classification features signals for each of said plurality of individuals.

16. An apparatus according to claim 15 in which said stimulator provides a first series of stimulation events for each of said plurality of individuals to evoke a first series of event related patterns of physiological activity generated in the brain for each of said plurality of individuals, said at least one sensor adapted to be operatively disposed with respect to the scalp or skin of each of said plurality of individuals provides a first series of signals representative of said first series of first event related patterns of physiological activity generated in the brain of each of said plurality of individuals and said data acquisition/transformation stage coupled to receive said first series of signals representative of said first series of first event related patterns of said physiological activity generated in the brain of each of said plurality of individuals is adapted to transform said first series of signals representative of said first event related patterns of physiological activity generated in the brain of each of said plurality of individuals into first patterns classification feature signals representative of said first event related patterns of physiological activity generated in the brain of each of said plurality of individuals, said data acquisition/transformation stage being further adapted to store said first patterns classification feature signals representative of said patterns of physiological activity generated in the brain of each of said plurality of individuals.

17. An apparatus according to claim 14, said stimulator provides a first series of stimulation events to evoke a first series of event related patterns of physiological activity generated in the brain, said at least one sensor adapted to be operatively disposed with respect to the scalp or skin of said individual provides a first series of signals representative of said first series of first event related patterns of physiological activity generated in the brain and said data acquisition/transformation stage coupled to receive said first series of signals representative of said first series of first event related patterns of said physiological activity generated in the brain is adapted to transform said first series of signals representative of said first event related patterns of physiological activity generated in the brain into first patterns clarification feature signals representative of said first event related patterns of physiological activity generated in the brain of said individual, said data acquisition/transformation stage being further adapted to store said first patterns classification feature signals of said individual.

18. An apparatus according to claim 17 in which said stimulator includes a monitor and a computer coupled to said data acquisition/transformation stage to effect said first stimulation events of said individual in a predetermined time sequence with respect to the evoked said first series of event related patterns of physiological activity generated in the brain of said individual.

19. An apparatus according to claim 18 in which said at least one sensor is at least one pair of a sensor electrode and a reference electrode for sensing event-related potentials.

20. An apparatus according to claim 19 in which said at least one sensor is a plurality of pairs of sensor electrodes and reference electrodes for sensing event-related potentials.

21. An apparatus according to claim 18 in which said at least one sensor is at least one sensor coil for sensing event-related fields.

22. An apparatus according to claim 18 in which said at least one sensor is at least one sensor coil for sensing event-related fields.

23. An apparatus according to claim 18 in which said at least one sensor is a plurality of sensor coils for sensing event-related fields.

24. An apparatus for indicating a brain impaired condition of an identified individual based upon data representing at least one pattern of physiological activity generated in the brain of said individual comprising:
a stimulator located with respect to said individual to provide a first stimulation event which includes at least one stimulus for said individual to evoke a first event related pattern of physiological activity generated in the brain;

at least one sensor adapted to be operatively disposed with respect to the scalp or skin of said individual that provides signals representative of said first event related pattern of physiological activity generated in the brain; and a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual to indicate the identification thereof, said data acquisition/transformation stage being further adapted to provide a memory to store said first pattern classification feature signals of said first event related pattern of physiological activity generated in the brain of said individual, said stimulator being adapted to provide a subsequent stimulation event which includes at least one stimulus for said individual to evoke a subsequent related pattern of physiological activity generated in the brain, said at least one sensor being adapted to be operatively disposed with respect to the scalp or skin of said individual to provide signals representative of said subsequent event related pattern of physiological activity generated in the brain, and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate a brain impaired condition of said individual, said data acquisition/transformation stage includes a neural network adapted to transform said signals representative of said first event related pattern of physiological activity generated in the brain and said subsequent event related pattern of physiological activity generated in the brain to create, train and test said neural network to distinguish said first pattern classification features signals and said subsequent pattern classification feature signals of said individual.

25. An apparatus according to claim 24 in which said neural network to distinguish said first pattern classification feature signals and said subsequent pattern classification feature signals of said individual, said neural network of said data acquisition/transformation stage is adapted to transform said signals representative of said first event related pattern of physiological activity generated in the brain and subsequent event related pattern of physiological activity generated in the brain from a plurality of individuals to create, train and test said neural network to distinguish said first pattern classification features signals and said subsequent pattern classification feature signals for each of said plurality of individuals.

26. An apparatus according to claim 25 in which said stimulator provides a first series of stimulation events for each of said plurality of individuals to evoke a first series of event related patterns of physiological activity generated in the brain for each of said plurality of individuals, said at least one sensor adapted to be operatively disposed with respect to the scalp or skin of each of said plurality of individuals provides a first series of signals representative of said first series of first event related patterns of physiological activity generated in the brain of each of said plurality of individuals and said data acquisition/transformation stage coupled to receive said first series of signals representative of said first series of first event related patterns of said physiological activity generated in the brain of each of said plurality of individuals is adapted to transform said first series of signals representative of said first event related patterns of physiological activity generated in the brain of each of said plurality of individuals into first patterns clarification feature signals representative of said first event related patterns of physiological activity generated in the brain of each of said plurality of individuals, said data acquisition/transformation stage being further adapted to store said first patterns classification feature signals representative of said patterns of physiological activity generated in the brain of each of said plurality of individuals.

27. An apparatus according to claim 24, said stimulator provides a first series of stimulation events to evoke a first series of event related patterns of physiological activity generated in the brain, said at least one sensor adapted to be operatively disposed with respect to the scalp or skin of said individual provides a first series of signals representative of said first series of first event related patterns of physiological activity generated in the brain and said data acquisition/transformation stage coupled to receive said first series of signals representative of said first series of first event related patterns of said physiological activity generated in the brain is adapted to transform said first series of signals representative of said first event related patterns of physiological activity generated in the brain into first patterns classification feature signals representative of said first event related patterns of physiological activity generated in the brain of said individual, said data acquisition/transformation stage being further adapted to store said first patterns classification feature signals of said individual.

28. An apparatus according to claim 27 in which said stimulator includes a monitor and a computer coupled to said data acquisition/transformation stage to effect said first stimulation events of said individual in a predetermined time sequence with respect to the evoked said first series of event related patterns of physiological activity generated in the brain of said individual.

29. An apparatus according to claim 28 in which said at least one sensor is at least one pair of a sensor electrode and a reference electrode for sensing event-related potentials.

30. An apparatus according to claim 29 in which said at least one sensor is a plurality of pairs of sensor electrodes and reference electrodes for sensing event-related potentials.

31. An apparatus according to claim 28 in which said at least one sensor is at least one sensor coil for sensing event-related fields.

32. An apparatus according to claim 28 in which said at least one sensor is at least one sensor coil for sensing event-related fields.

33. An apparatus according to claim 28 in which said at least one sensor is a plurality of sensor coils for sensing event-related fields.

34. An apparatus for identifying an individual based upon data representing at least one pattern of physiological activity generated in the brain of said individual comprising:

a stimulator located with respect to said individual to provide a first stimulation event which includes at least one stimulus for said individual to evoke a first event related pattern of physiological activity generated in the brain;

at least one sensor adapted to be operatively disposed with respect to the scalp or skin of said individual that provides signals representative of said first event related pattern of physiological activity generated in the brain; and a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual, said data acquisition/transformation stage being further adapted to provide a memory to store said first pattern classification feature signals of said first event related pattern of physiological activity generated in the brain of said individual, said stimulator being adapted to provide a subsequent stimulation event which includes at least one stimulus for said individual to evoke a subsequent event related pattern of physiological activity generated in the brain, said at least one sensor being adapted to be operatively disposed with respect to the scalp or skin of said individual to provide signals representative of said subsequent event related pattern of physiological activity generated in the brain and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate the identification thereof, said data acquisition/transformation stage includes a first computer having a neural network being suitably programmed to transform said signals representative of said first event related pattern of physiological activity generated in the brain and said subsequent event related pattern of physiological activity generated in the brain to create, train and test said neural network to distinguish said first pattern classification feature signals and said subsequent pattern classification feature signals of said individual.

35. An apparatus according to claim 34, in which said neural network of said computer of said data acquisition/transformation stage is suitably programmed to transform said signals representative of said first event related pattern of physiological activity generated in the brain and subsequent event related pattern of physiological activity generated in the brain from a plurality of individuals to create, train and test said neural network to distinguish said first pattern classification feature signals and said subsequent pattern classification feature signals for each of said plurality of individuals.

36. An apparatus according to claim 35 in which said stimulator provides a first series of stimulation events for each of said plurality of individuals to evoke a first series of event related patterns of physiological activity generated in the brain for each of said plurality of individuals, said at least one sensor adapted to be operatively disposed with respect to the scalp or skin of each of said plurality of individuals provides a first series of signals representative of said first series of first event related patterns of physiological activity generated in the brain of each of said plurality of individuals and said data acquisition/transformation stage coupled to receive said first series of signals representative of said first series of first event related patterns of said physiological activity generated in the brain of each of said plurality of individuals is adapted to transform said first series of signals representative of said first event related patterns of physiological activity generated in the brain of each of said plurality of individuals into first patterns classification feature signals representative of said first event related patterns of physiological activity generated in the brain of each of said plurality of individuals, said data acquisition/transformation stage being further adapted to store said first patterns classification feature signals representative of said patterns of physiological activity generated in the brain of each of said plurality of individuals.

37. An apparatus according to claim 34 in which said stimulator provides a first series of stimulation events to evoke a first series of event related patterns of physiological activity generated in the brain, said at least one sensor adapted to be operatively disposed with respect to the scalp or skin of said individual provides a first series of signals representative of said first series of first event related patterns of physiological activity generated in the brain and said data acquisition/transformation stage coupled to receive said first series of signals representative of said first series of first event related patterns of physiological activity generated in the brain is adapted to transform said first series of signals representative of said first event related patterns of physiological activity generated in the brain into first patterns classification feature signals representative of said first event related patterns of physiological activity generated in the brain of said individual, said data acquisition/transformation stage being further adapted to store said first patterns classification feature signals of said individual.

38. An apparatus according to claim 37 in which said stimulator includes a monitor and a computer coupled to said data acquisition/transformation stage to effect said first stimulation events of said individual in a predetermined time sequence with respect to the evoked said first series of event related patterns of physiological activity generated in the brain of said individual.

39. An apparatus according to claim 38 in which said at least one sensor is at least one pair of a sensor electrode and a reference electrode for sensing event-related potentials.

40. An apparatus according to claim 38 in which said at least one sensor is a plurality of pairs of sensor electrodes and reference electrodes for sensing event-related potentials.

41. An apparatus according to claim 38 in which said at least one sensor is a plurality of sensor coils for sensing event-related fields.

42. An apparatus for indicating a brain impaired condition of an identified individual based upon data representing at least one pattern of physiological activity generated in the brain of said individual comprising:

a stimulator located with respect to said individual to provide a first stimulation event which includes at least one stimulus for said individual to evoke a first event related pattern of physiological activity generated in the brain;

at least one sensor adapted to be operatively disposed with respect to the scalp or skin of said individual that provides signals representative of said first event related pattern of physiological activity generated in the brain; and a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual, said data acquisition/transformation stage being further adapted to provide a memory to store said first pattern classification feature signals of said first event related pattern of physiological activity generated in the brain of said individual, said stimulator being adapted to provide a subsequent stimulation event which includes at least one stimulus for said individual to evoke a subsequent related pattern of physiological activity generated in the brain, said at least one sensor being adapted to be operatively disposed with respect to the scalp or skin of said individual to provide signals representative of said subsequent event related pattern of physiological activity generated in the brain, and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate a brain impaired condition of said individual, said data acquisition/transformation stage includes a first computer having a neural network being suitably programmed to transform said signals representative of said first event related pattern of physiological activity generated in the brain and said subsequent event related pattern of physiological activity generated in the brain to create, train and test said neural network to distinguish said first pattern classification feature signals and said subsequent pattern classification feature signals of said individual.

43. An apparatus according to claim 42, in which said neural network of said computer of said data acquisition/transformation stage is suitably programmed to transform said signals representative of said first event related pattern of physiological activity generated in the brain and subsequent event related pattern of physiological activity generated in the brain from a plurality of individuals to create, train and test said neural network to distinguish said first pattern classification feature signals and said subsequent pattern classification feature signals for each of said plurality of individuals.

44. An apparatus according to claim 43 in which said stimulator provides a first series of stimulation events for each of said plurality of individuals to evoke a first series of event related patterns of physiological activity generated in the brain for each of said plurality of individuals, said at least one sensor adapted to be operatively disposed with respect to the scalp or skin of each of said plurality of individuals provides a first series of signals representative of said first series of first event related patterns of physiological activity generated in the brain of each of said plurality of individuals and said data acquisition/transformation stage coupled to receive said first series of signals representative of said first series of first event related patterns of said physiological activity generated in the brain of each of said plurality of individuals is adapted to transform said first series of signals representative of said first event related patterns of physiological activity generated in the brain of each of said plurality of individuals into first patterns classification feature signals representative of said first event related pattern of physiological activity generated in the brain of each of said plurality of individuals, said data acquisition/transformation stage being further adapted to store said first patterns classification feature signals representative of said patterns of physiological activity generated in the brain of each of said plurality of individuals.

45. An apparatus according to claim 42 in which said stimulator provides a first series of stimulation events to evoke a first series of event related patterns of physiological activity generated in the brain, said at least one sensor adapted to be operatively disposed with respect to the scalp or skin of said individual provides a first series of signals representative of said first series of first event related patterns of physiological activity generated in the brain and said data acquisition/transformation stage coupled to receive said first series of signals representative of said first series of first event related patterns of said physiological activity generated in the brain is adapted to transform said first series of signals representative of said first event related patterns of physiological activity generated in the brain into first patterns classification feature signals representative of said first event related patterns of physiological activity generated in the brain of said individual, said data acquisition/transformation stage being further adapted to store said first patterns classification feature signals of said individual.

46. An apparatus according to claim 45 in which said stimulator includes a monitor and a computer coupled to said data acquisition/transformation stage to effect said first stimulation events of said individual in a predetermined time sequence with respect to the evoked said first series of event related patterns of physiological activity generated in the brain of said individual.

47. An apparatus according to claim 46 in which said at least one sensor is at least one pair of a sensor electrode and a reference electrode for sensing event-related potentials.

48. An apparatus according to claim 46 in which said at least one sensor is a plurality of pairs of sensor electrodes and reference electrodes for sensing event-related potentials.

49. An apparatus according to claim 46 in which said at least one sensor is a plurality of sensor coils for sensing event-related fields.

50. An apparatus for identifying an individual based upon data representing at least one pattern of physiological activity generated in the brain of said individual comprising:
 a stimulator located with respect to said individual to provide a first stimulation event which includes at least one stimulus for said individual to evoke a first event related pattern of physiological activity generated in the brain;
 at least one sensor adapted to be operatively disposed with respect to the scalp or skin of said individual that provides signals representative of said first event related pattern of physiological activity generated in the brain; and
 a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual, said data acquisition/transformation stage being further adapted to provide a memory to store said first pattern classification feature signals of said first event related pattern of physiological activity generated in the brain of said individual, said stimulator being adapted to provide a subsequent stimulation event which includes at least one stimulus for said individual to evoke a subsequent event related pattern of physiological activity generated in the brain, said at least one sensor being adapted to be operatively disposed with respect to the scalp or skin of said individual to provide signals representative of said subsequent event related pattern of physiological activity generated in the brain and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate the identification thereof, said stimulator provides a first series of stimulation events to evoke a first series of event related patterns of physiological activity generated in the brain, said at least one sensor adapted to be operatively disposed with respect to the scalp or skin of said individual provides a first series of signals representative of said first series of first event related patterns of physiological activity generated in the brain and said data acquisition/transformation stage coupled to receive said first series of signals representative of said first series of first event related patterns of said physiological activity generated in the brain is adapted to transform said first series of signals representative of said first event related patterns of physiological activity generated in the brain into first patterns classification feature signals representative of said first event related patterns of physiological activity generated in the brain of said individual, said data acquisition/transformation stage being further adapted to store said first classification feature signals of said individual and said stimulator includes a monitor and a computer coupled to said data acquisition/transformation stage to effect said first stimulation events of said individual in a predetermined time sequence with respect to the evoked said first series of event related patterns of physiological activity generated in the brain of said individual.

51. An apparatus for indicating a brain impaired condition of an identified individual based upon data representing at least one pattern of physiological activity generated in the brain of said individual comprising:
 a stimulator located with respect to said individual to provide a first stimulation event which includes at least one stimulus for said individual to evoke a first event related pattern of physiological activity generated in the brain;
 at least one sensor adapted to be operatively disposed with respect to the scalp or skin of said individual that provides signals representative of said first event related pattern of physiological activity generated in the brain; and
 a data acquisition/transformation stage coupled to receive said signals representative of said first event related pattern of physiological activity generated in the brain being adapted to transform said signals representative of said first event related pattern of physiological activity generated in the brain into first pattern classification feature signals representative of said first event related pattern of physiological activity generated in the brain of said individual, said data acquisition/transformation stage being further adapted to provide a memory to store said first pattern classification feature signals of said first event related pattern of physiological activity generated in the brain of said individual, said stimulator being adapted to provide a subsequent stimulation event which includes at least one stimulus for said individual to evoke a subsequent related pattern of physiological activity generated in the brain, said at least one sensor being adapted to be operatively disposed with respect to the scalp or skin of said individual to provide signals representative of said subsequent event related pattern of physiological activity generated in the brain, and said data acquisition/transformation stage being adapted to transform said signals representative of said subsequent event related pattern of physiological activity generated in the brain into subsequent pattern classification feature signals representative of said subsequent event related pattern of physiological activity generated in the brain of said individual, said data acquisition/transformation stage being further adapted to compare the stored said first pattern classification feature signals of said first event related pattern of physiological activity generated in the brain of said individual with said subsequent pattern classification feature signals representative of said subsequent event related pattern of physiological activity generated in the brain of said individual to indicate a brain impaired condition of said individual, said stimulator provides a first series of stimulation events to evoke a first series of event related patterns of physiological activity generated in the brain, said at least one sensor adapted to be operatively disposed with respect to the scalp or skin of said individual provides a first series of signals representative of said first series of first event related patterns of physiological activity generated in the brain and said data acquisition/transformation stage coupled to receive said first series of signals representative of said first series of first event related patterns of said physiological activity generated in the brain is adapted to transform said first series of signals representative of said first event related patterns of physiological activity generated in the brain into first patterns classification feature signals representative of said first event related patterns of physiological activity generated in the brain of said individual, said data acquisition/transformation stage being further adapted to store said first classification feature signals of said individual and said stimulator includes a monitor and a computer coupled to said data acquisition/transformation stage to effect said first stimulation events of said individual in a predetermined time sequence with respect to the evoked said first series of event related patterns of physiological activity generated in the brain of said individual.

52. A method of identifying an individual based upon data representing at least one pattern of physiological activity generated in the brain of said individual comprising:
a first stimulating of said individual with a first stimulation event which includes at least one stimulus to evoke a first event related pattern of physiological activity generated in the brain;
a first sensing of signals representative of said first event related pattern of physiological activity generated in the brain with a sensor adapted to be operatively disposed with respect to the scalp or skin of said individual;
a first receiving of said signals representative of said first event related pattern of physiological activity generated in the brain in a data acquisition/transformation stage;
a first transforming of said signals representative of said first event related pattern of physiological activity generated in the brain into first pattern classification feature signals representative of said pattern of physiological activity generated in the brain of said individual in said data acquisition/transformation stage;
providing memory in said data acquisition/transformation stage to store said first pattern classification feature signals of said first event related pattern of physiological activity generated in the brain of said individual;
subsequently stimulating said individual with a subsequent stimulation event which includes at least one stimulus for said individual to evoke a subsequent event related pattern of physiological activity generated in the brain;
subsequently sensing said subsequent event related pattern of physiological activity generated in the brain with said sensor adapted to be operatively disposed with respect to the scalp or skin of said individual to provide signals representative of said subsequent event related pattern of physiological activity generated in the brain;
subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and
comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate the identification thereof, said transforming is performed by a neural network in said data acquisition/transformation stage that transforms said signals representative of said first event related pattern of physiological activity generated in the brain and said subsequent event related pattern of physiological activity generated in the brain to create, train and test said neural network to distinguish said first pattern classification feature signals and said subsequent pattern classification feature signals of said individual.

53. A method according to claim 52, in which said transforming is performed by said neural network of said data acquisition/transformation stage that transforms said signals representative of said first event related pattern of physiological activity generated in the brain and subsequent event related pattern of physiological activity generated in the brain from a plurality of individuals to create, train and test said neural network to distinguish said first pattern classification feature signals and said subsequent pattern classification feature signals for each of said plurality of individuals.

54. A method of indicating a brain impaired condition of an identified individual based upon data representing at least one pattern of physiological activity generated in the brain of said individual comprising:
a first stimulating of said individual with a first stimulation event which includes at least one stimulus to evoke a first event related pattern of physiological activity generated in the brain;

a first sensing of signals representative of said first event related pattern of physiological activity generated in the brain with a sensor adapted to be operatively disposed with respect to the scalp or skin of said individual;

a first receiving of said signals representative of said first event related pattern of physiological activity generated in the brain in a data acquisition/transformation stage;

a first transforming of said signals representative of said first event related pattern of physiological activity generated in the brain into first pattern classification feature signals representative of said pattern of physiological activity generated in the brain of said individual in said data acquisition/transformation stage;

providing memory in said data acquisition/transformation stage to store said first pattern classification feature signals of said first event related pattern of physiological activity generated in the brain of said individual;

subsequently stimulating said individual with a subsequent stimulation event which includes at least one stimulus for said individual to evoke a subsequent event related pattern of physiological activity generated in the brain;

subsequently sensing said subsequent event related pattern of said physiological activity generated in the brain with a sensor adapted to be operatively disposed with respect to the scalp or skin of said individual to provide signals representative of said subsequent event related pattern of physiological activity generated in the brain;

subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate a brain impaired condition thereof, said transforming is performed by a neural network in said data acquisition/transformation stage that transforms said signals representative of said first event related pattern of physiological activity generated in the brain and said subsequent event related pattern of physiological activity generated in the brain to create, train and test said neural network to distinguish said first pattern classification feature signals and said subsequent pattern classification feature signals of said individual.

55. A method according to claim 54, in which said transforming is performed by said neural network of said data acquisition/transformation stage that transforms said signals representative of said first event related pattern of physiological activity generated in the brain and subsequent event related pattern of physiological activity generated in the brain from a plurality of individuals to create, train and test said neural network to distinguish said first pattern classification feature signals and said subsequent pattern classification feature signals for each of said plurality of individuals.

56. A method of identifying an individual based upon data representing at least one pattern of physiological activity generated in the brain of said individual comprising:

a first stimulating of said individual with a first stimulation event which includes at least one stimulus to evoke a first event related pattern of physiological activity generated in the brain;

a first sensing of signals representative of said first event related pattern of physiological activity generated in the brain with a sensor adapted to be operatively disposed with respect to the scalp or skin of said individual;

a first receiving of said signals representative of said first event related pattern of physiological activity generated in the brain in a data acquisition/transformation stage;

a first transforming of said signals representative of said first event related pattern of physiological activity generated in the brain into first pattern classification feature signals representative of said pattern of physiological activity generated in the brain of said individual in said data acquisition/transformation stage;

providing memory in said data acquisition/transformation stage to store said first pattern classification feature signals of said first event related pattern of physiological activity generated in the brain of said individual;

subsequently stimulating said individual with a subsequent stimulation event which includes at least one stimulus for said individual to evoke a subsequent event related pattern of physiological activity generated in the brain;

subsequently sensing said subsequent event related pattern of physiological activity generated in the brain with said sensor adapted to be operatively disposed with respect to the scalp or skin of said individual to provide signals representative of said subsequent event related pattern of physiological activity generated in the brain;

subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate the identification thereof, said transforming is performed by a suitably programmed first computer having a neural network in said data acquisition/transformation stage that transforms said signals representative of said first event related pattern of physiological activity generated in the brain and said subsequent event related pattern of physiological activity generated in the brain to create, train and test said neural network to distinguish said first pattern classification feature signals and subsequent pattern classification feature signals of said individual.

57. A method of indicating a brain impaired condition of an identified individual based upon data representing at least one pattern of physiological activity generated in the brain of said individual comprising:

a first stimulating of said individual with a first stimulation event which includes at least one stimulus to evoke a first event related pattern of physiological activity generated in the brain;

a first sensing of signals representative of said first event related pattern of physiological activity generated in the brain with a sensor adapted to be operatively disposed with respect to the scalp or skin of said individual;

a first receiving of said signals representative of said first event related pattern of physiological activity generated in the brain in a data acquisition/transformation stage;

a first transforming of said signals representative of said first event related pattern of physiological activity generated in the brain into first pattern classification feature signals representative of said pattern of physiological activity generated in the brain of said individual in said data acquisition/transformation stage;

providing memory in said data acquisition/transformation stage to store said first pattern classification feature signals of said first event related pattern of physiological activity generated in the brain of said individual;

subsequently stimulating said individual with a subsequent stimulation event which includes at least one stimulus for said individual to evoke a subsequent event related pattern of physiological activity generated in the brain;

subsequently sensing said subsequent event related pattern of said physiological activity generated in the brain with a sensor adapted to be operatively disposed with respect to the scalp or skin of said individual to provide signals representative of said subsequent event related pattern of physiological activity generated in the brain;

subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate a brain impaired condition thereof, said transforming is performed by a suitably programmed first computer having a neural network in said data acquisition/transformation stage that transforms said signals representative of said first event related pattern of physiological activity generated in the brain and said subsequent event related pattern of physiological activity generated in the brain to create, train and test said neural network to distinguish said first pattern classification feature signals and said subsequent pattern classification feature signals of said individual.

58. A method of identifying an individual based upon data representing at least one pattern of physiological activity generated in the brain of said individual comprising:

a first stimulating of said individual with a first stimulation event which includes at least one stimulus to evoke a first event related pattern of physiological activity generated in the brain;

a first sensing of signals representative of said first event related pattern of physiological activity generated in the brain with a sensor adapted to be operatively disposed with respect to the scalp or skin of said individual;

a first receiving of said signals representative of said first event related pattern of physiological activity generated in the brain in a data acquisition/transformation stage;

a first transforming of said signals representative of said first event related pattern of physiological activity generated in the brain into first pattern classification feature signals representative of said pattern of physiological activity generated in the brain of said individual in said data acquisition/transformation stage;

providing memory in said data acquisition/transformation stage to store said first pattern classification feature signals of said first event related pattern of physiological activity generated in the brain of said individual;

subsequently stimulating said individual with a subsequent stimulation event which includes at least one stimulus for said individual to evoke a subsequent event related pattern of physiological activity generated in the brain;

subsequently sensing said subsequent event related pattern of physiological activity generated in the brain with said sensor adapted to be operatively disposed with respect to the scalp or skin of said individual to provide signals representative of said subsequent event related pattern of physiological activity generated in the brain;

subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate the identification thereof, said transforming is performed by a suitably programmed first computer having a neural network in said data acquisition/transformation stage that transforms said signals representative of said first event related pattern of physiological activity generated in the brain and said subsequent event related pattern of physiological activity generated in the brain to create, train and test said neural network to distinguish said first pattern classification feature signals and said subsequent pattern classification feature signals of said individual, said transforming is performed by a suitably programmed said neural network of said computer of said data acquisition/transformation stage that transforms said signals representative of said first event related pattern of physiological activity generated in the brain and subsequent event related pattern of physiological activity generated in the brain from a plurality of individuals to create, train and test said neural network to distinguish said first pattern classification feature signals and said subsequent pattern classification feature signals for each of said plurality of individuals.

59. A method of indicating a brain impaired condition of an identified individual based upon data representing at least one pattern of physiological activity generated in the brain of said individual comprising:
- a first stimulating of said individual with a first stimulation event which includes at least one stimulus to evoke a first event related pattern of physiological activity generated in the brain;
- a first sensing of signals representative of said first event related pattern of physiological activity generated in the brain with a sensor adapted to be operatively disposed with respect to the scalp or skin of said individual;
- a first receiving of said signals representative of said first event related pattern of physiological activity generated in the brain in a data acquisition/transformation stage;
- a first transforming of said signals representative of said first event related pattern of physiological activity generated in the brain into first pattern classification feature signals representative of said pattern of physiological activity generated in the brain of said individual in said data acquisition/transformation stage;
- providing memory in said data acquisition/transformation stage to store said first pattern classification feature signals of said first event related pattern of physiological activity generated in the brain of said individual;
- subsequently stimulating said individual with a subsequent stimulation event which includes at least one stimulus for said individual to evoke a subsequent event related pattern of
- subsequently sensing said subsequent event related pattern of said physiological activity generated in the brain with a sensor adapted to be operatively disposed with respect to the scalp or skin of said individual to provide signals representative of said subsequent event related pattern of physiological activity generated in the brain;
- subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and
- comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate a brain impaired condition thereof, said transforming is performed by a suitably programmed first computer having a neural network in said data acquisition/transformation stage that transforms said signals representative of said first event related pattern of physiological activity generated in the brain and said subsequent event related pattern of physiological activity generated in the brain to create, train and test said neural network to distinguish said first pattern classification feature signals and said subsequent pattern classification feature signals of said individual, said transforming is performed by a suitably programmed said neural network of said computer of said data acquisition/transformation stage that transforms said signals representative of said first event related pattern of physiological activity generated in the brain and subsequent event related pattern of physiological activity generated in the brain from a plurality of individuals to create, train and test said neural network to distinguish said first pattern classification feature signals and said subsequent pattern classification feature signals for each of said plurality of individuals.

60. A method of identifying an individual based upon data representing at least one pattern of physiological activity generated in the brain of said individual comprising:
- a first stimulating of said individual with a first stimulation event which includes at least one stimulus to evoke a first event related pattern of physiological activity generated in the brain;
- a first sensing of signals representative of said first event related pattern of physiological activity generated in the brain with a sensor adapted to be operatively disposed with respect to the scalp or skin of said individual;
- a first receiving of said signals representative of said first event related pattern of physiological activity generated in the brain in a data acquisition/transformation stage;
- a first transforming of said signals representative of said first event related pattern of physiological activity generated in the brain into first pattern classification feature signals representative of said pattern of physiological activity generated in the brain of said individual in said data acquisition/transformation stage;
- providing memory in said data acquisition/transformation stage to store said first pattern classification feature signals of said first event related pattern of physiological activity generated in the brain of said individual;
- subsequently stimulating said individual with a subsequent stimulation event which includes at least one stimulus for said individual to evoke a subsequent event related pattern of physiological activity generated in the brain;
- subsequently sensing said subsequent event related pattern of physiological activity generated in the brain with said sensor adapted to be operatively disposed with respect to the scalp or skin of said individual to provide signals representative of said subsequent event related pattern of physiological activity generated in the brain;

subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate the identification thereof, said first stimulating is the providing of a first series of stimulation events to evoke a first series of event related patterns of physiological activity generated in the brain, said first sensing by at least one sensor adapted to be operatively disposed with respect to the scalp or skin of said individual provides a first series of signals representative of said first series of first event related patterns of physiological activity generated in the brain, said first transforming is by said data acquisition/transformation stage that transforms said first series of signals representative of said first series of first event related patterns of physiological activity generated in the brain into first patterns classification feature signals representative of said first event related patterns of physiological activity generated in the brain of said individual and said providing memory is the storing of said first pattern classification feature signals of said individual.

61. A method of identifying a brain impaired condition of an identified individual based upon data representing at least one pattern of physiological activity generated in the brain of said individual comprising:

a first stimulating of said individual with a first stimulation event which includes at least one stimulus to evoke a first event related pattern of physiological activity generated in the brain;

a first sensing of signals representative of said first event related pattern of physiological activity generated in the brain with a sensor adapted to be operatively disposed with respect to the scalp or skin of said individual;

a first receiving of said signals representative of said first event related pattern of physiological activity generated in the brain in a data acquisition/transformation stage;

a first transforming of said signals representative of said first event related pattern of physiological activity generated in the brain into first pattern classification feature signals representative of said pattern of physiological activity generated in the brain of said individual in said data acquisition/transformation stage;

providing memory in said data acquisition/transformation stage to store said first pattern classification feature signals of said first event related pattern of physiological activity generated in the brain of said individual;

subsequently stimulating said individual with a subsequent stimulation event which includes at least one stimulus for said individual to evoke a subsequent event related pattern of physiological activity generated in the brain;

subsequently sensing said subsequent event related pattern of said physiological activity generated in the brain with a sensor adapted to be operatively disposed with respect to the scalp or skin of said individual to provide signals representative of said subsequent event related pattern of physiological activity generated in the brain;

subsequently transforming said signals representative of said subsequent event related pattern of physiological activity generated in the brain into subsequent pattern classification feature signals representative of said subsequent event related pattern of physiological activity generated in the brain of said individual in said data acquisition/transformation stage; and comparing the stored said first pattern classification feature signals of said first event related pattern of physiological activity generated in the brain of said individual with said subsequent pattern classification feature signals representative of said subsequent event related pattern of physiological activity generated in the brain of said individual in said data acquisition/transformation stage to indicate a brain impaired condition thereof, said first stimulating is the providing of a first series of stimulation events to evoke a first series of event related patterns of physiological activity generated in the brain, said first sensing by at least one sensor adapted to be operatively disposed with respect to the scalp or skin of said individual provides a first series of signals representative of said first series of first event related patterns of physiological activity generated in the brain, said first transforming is by said data acquisition/transformation stage that transforms said first series of signals representative of said first series of first event related patterns of physiological activity generated in the brain into first patterns classification feature signals representative of said first event related patterns of physiological activity generated in the brain of said individual and said providing memory is the storing of said first patterns classification feature signals of said individual.

* * * * *